United States Patent [19]
Sutter et al.

[11] Patent Number: 5,947,733
[45] Date of Patent: Sep. 7, 1999

[54] CONNECTOR BETWEEN AN IMPLANT AND AN ABUTMENT

[75] Inventors: Franz Sutter, Niederdorf; Vincenzo Grande, Möhlin; Roger Tschirky, Ettingen, all of Switzerland

[73] Assignee: Institut Straumann AG, Waldenburg, Switzerland

[21] Appl. No.: 08/836,589

[22] PCT Filed: Oct. 11, 1996

[86] PCT No.: PCT/CH95/00358

§ 371 Date: Sep. 29, 1997

§ 102(e) Date: Sep. 29, 1997

[87] PCT Pub. No.: WO97/14371

PCT Pub. Date: Apr. 24, 1997

[30] Foreign Application Priority Data

Oct. 13, 1995 [CH] Switzerland ............................ 2909/95
Aug. 19, 1996 [CH] Switzerland ............................ 2039/96

[51] Int. Cl.[6] ........................................... A61C 8/00
[52] U.S. Cl. .................................... 433/173; 433/174
[58] Field of Search ................................ 433/173, 174, 433/175, 176

[56] References Cited

U.S. PATENT DOCUMENTS

| 4,246,811 | 1/1981 | Bondhus et al. | 81/436 |
| 5,116,225 | 5/1992 | Riera | 433/173 |
| 5,302,126 | 4/1994 | Wimmer et al. | 433/173 |
| 5,322,443 | 6/1994 | Beaty | 433/173 |
| 5,334,024 | 8/1994 | Niznick | 433/173 |
| 5,368,483 | 11/1994 | Sutter et al. | 433/173 |
| 5,733,122 | 3/1998 | Gordon | 433/173 |

FOREIGN PATENT DOCUMENTS 94 17 182   2/1995   Germany .

*Primary Examiner*—Ralph A. Lewis
*Attorney, Agent, or Firm*—Selitto & Associates

[57] ABSTRACT

The connection arrangement between an implant (1) and a straight or angled abutment (800) can be produced using a clamping screw (400) and an expanding ring (500). An inlet (830) is provided in the abutment (800), and near the lower end of the abutment (800) this inlet (830) is widened via a radially encircling groove (835). The expanding ring (500) through which the clamping screw (400) passes is supported in the groove (835), the head (410) of the clamping screw (400) pressing on the expanding ring (500), and its threaded segment (430) engaging in the threaded bore (21) of the implant (1). The clamping screw (400) can be pushed from below into the inlet (830), with the expanding ring (500) pushed on and with the head (410) leading. The implant (1) can have a non-rotationally symmetrical receiving contour on the inner cone, primarily an inner polygon, and the abutment (800) advantageously has a counter-contour complementary to the receiving contour. A special screwdriver is used for screwing.

67 Claims, 9 Drawing Sheets

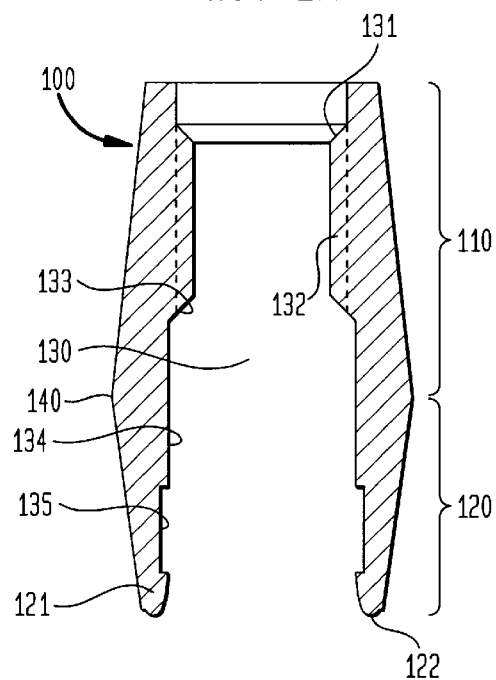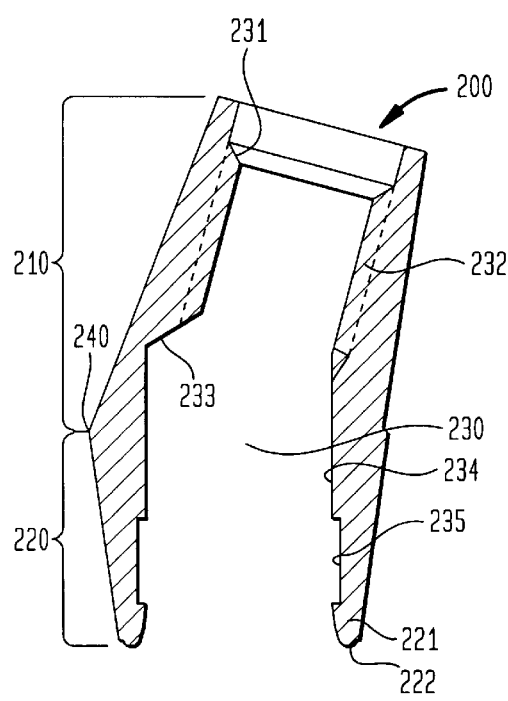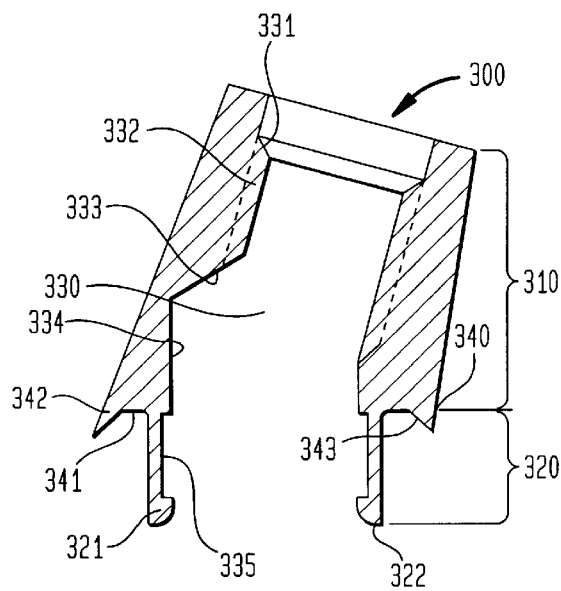

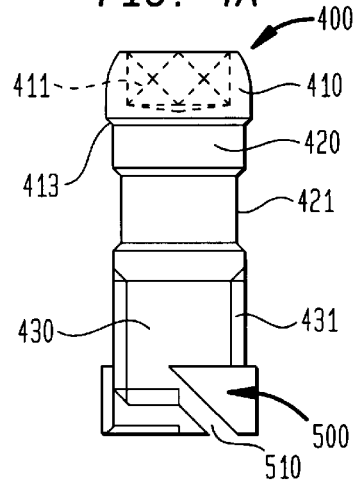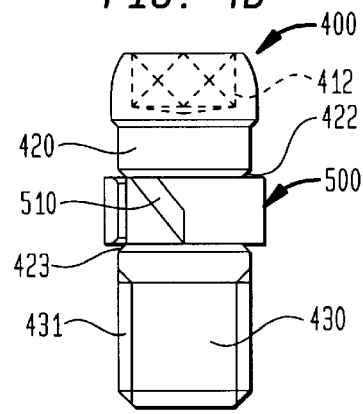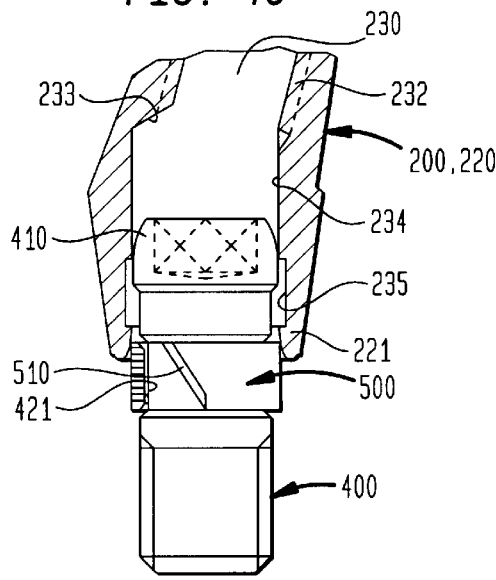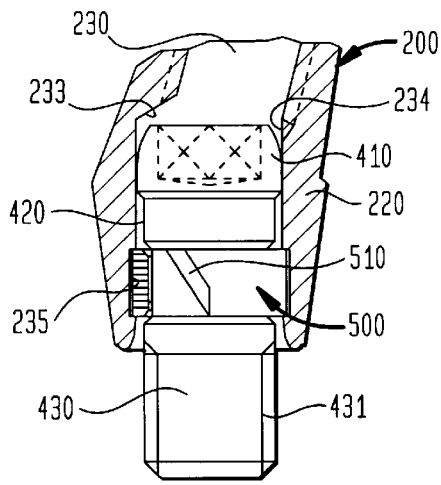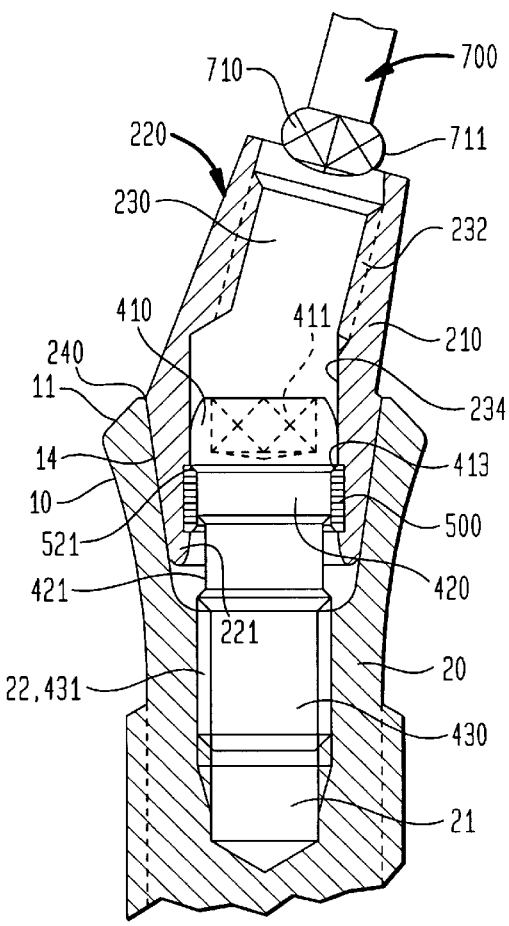

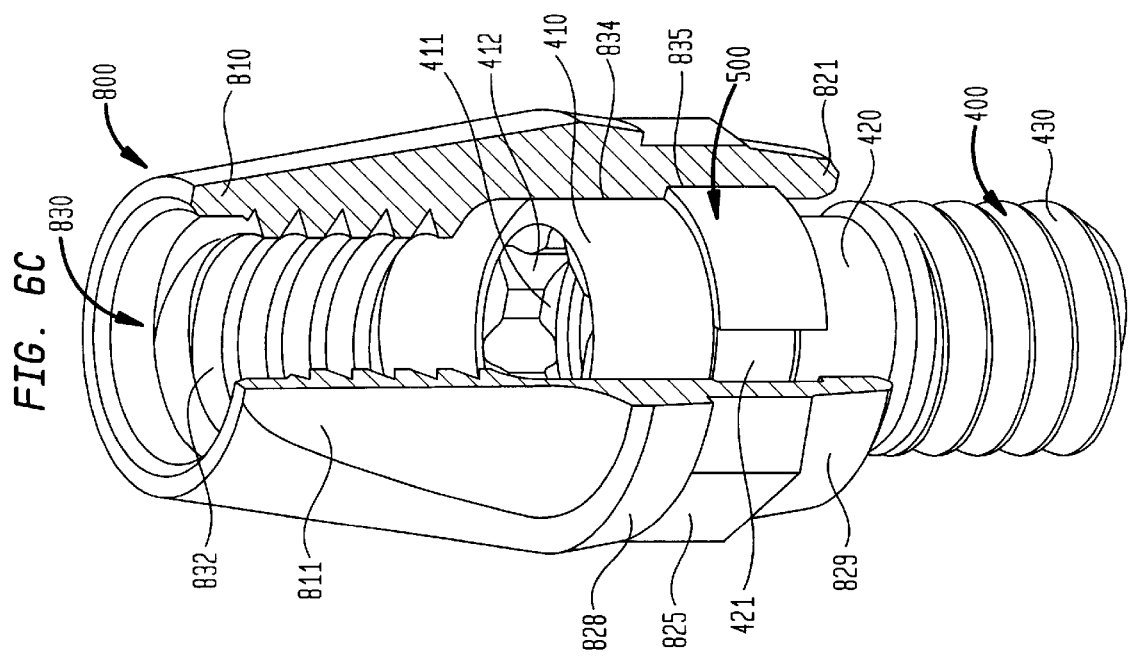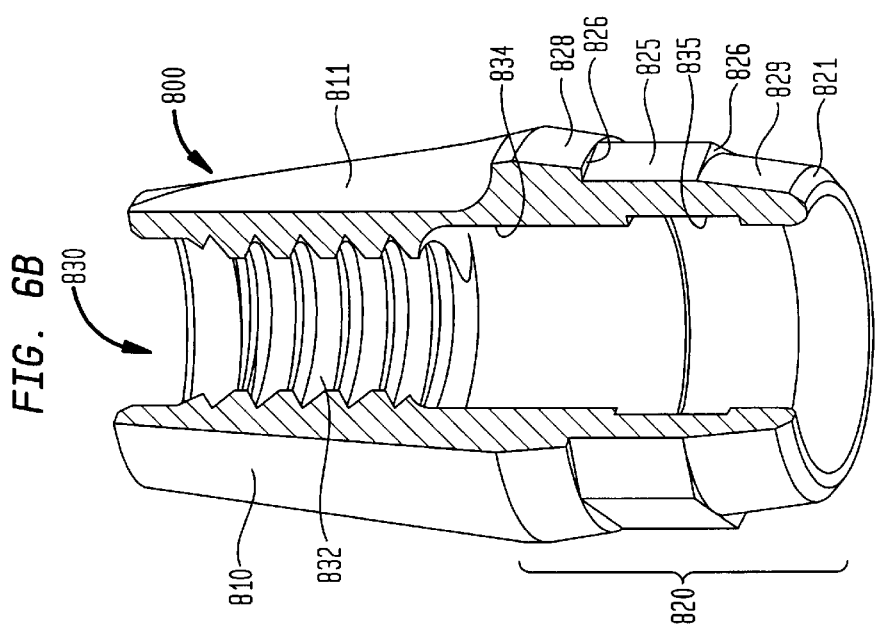

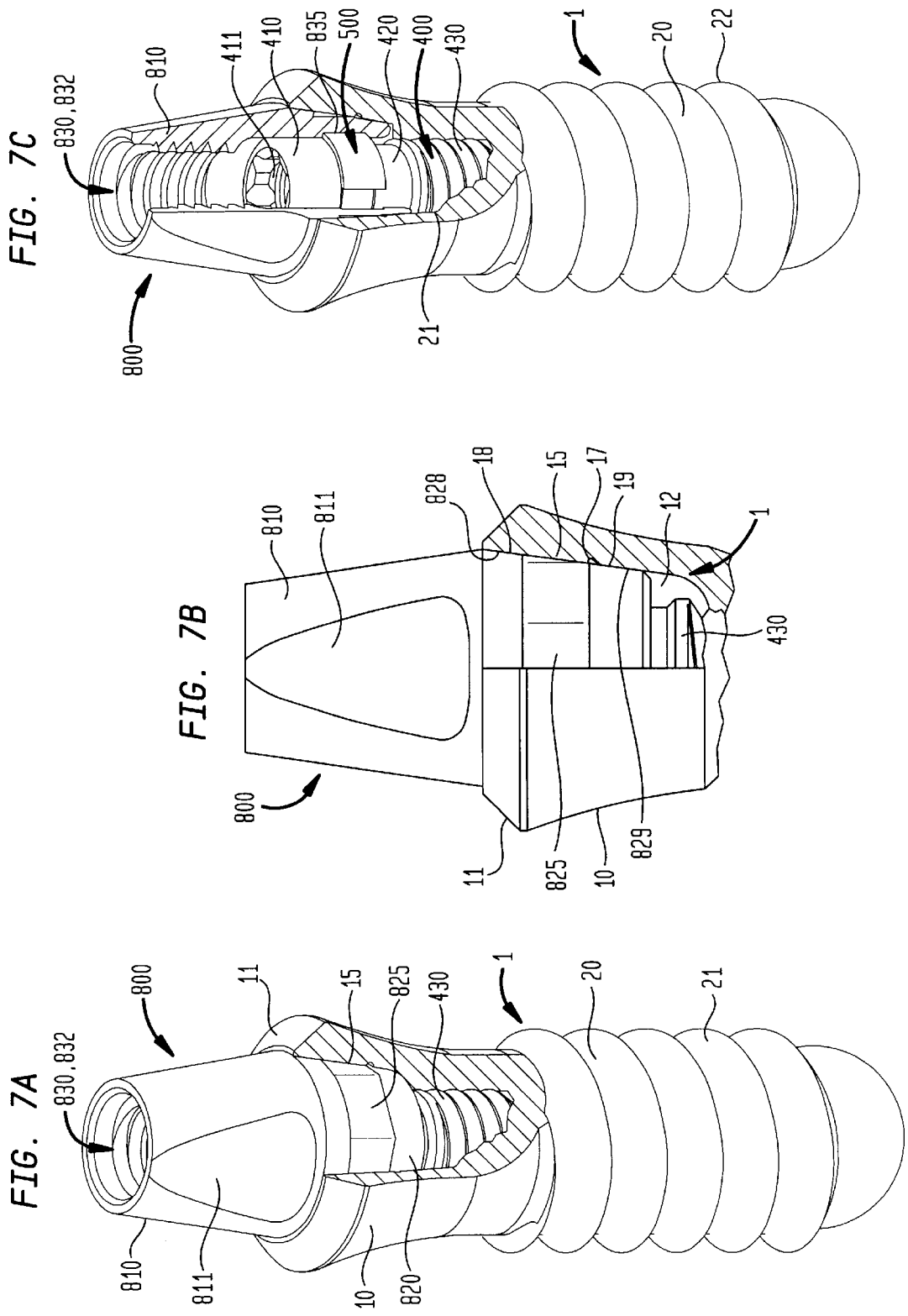

CONNECTOR BETWEEN AN IMPLANT AND AN ABUTMENT

FIELD OF APPLICATION OF THE INVENTION

The present invention relates to a connection arrangement for fixing an abutment in an implant which can be fitted in human bones, primarily a dental implant. Opening out at the top of the implant head is a receiving bore which extends axially downwards and which is conically widened towards the top and in which the lower and likewise conical root portion of the abutment sits. For securing the abutment in terms of rotation, a non-rotationally symmetrical receiving contour can be provided in the receiving bore. A coaxial, internally threaded bore extends from the bottom of the receiving bore. To complement the possible receiving contour in the implant, the root portion of the abutment can have a non-rotationally symmetrical outer contour.

Connection arrangements of this type are employed when using a straight or an angled abutment which is secured on the implant by means of a clamping screw, both axially and also against rotation. The clamping screw is introduced into the abutment so that the head of the clamping screw is supported in the abutment, while the threaded shank of the clamping screw protrudes from the abutment at the bottom and engages in the axial internal thread in the implant head. A special screwdriver which can be introduced into the inside of the abutment is provided for tightening and unscrewing the clamping screw, this screwdriver being used especially in the case of angled abutments, but also being suitable for straight abutments. The abutment can be fixed in any desired position of rotation, possible non-rotationally symmetrical contours on the implant and abutment limiting the selectable positions of rotation in accordance with the configuration of the contour of the polygon.

PRIOR ART

In its simplest form, a straight, conical abutment has at the very bottom a threaded plug which is screwed into the internally threaded bore present in the implant. The conical root portion of the abutment then sits in the conical receiving bore, and the head part of the abutment protrudes above the implant shoulder. No separate clamping screw is required here (cf. SCHROEDER, SUTTER, BUSER, KREKELER: Orale Implantologie [Oral implantology], Georg Thieme Verlag, Stuttgart, 2nd ed., 1994, page 122).
FIGS. 1A to 1D When using an angled abutment, the connection with the implant 1 has hitherto been based on providing the abutment with a lateral bore which extends vertically towards the seat of the clamping screw head and through which the screwdriver then has access to the clamping screw. The head of the clamping screw can be introduced via a lateral opening into the seat present in the abutment.

It is true that a connection arrangement of this type can be assembled and screwed together in a relatively practical way by means of the lateral bore and the lateral opening; however, as a result of the two material cutouts adjoining one another, a weak point is created in the wall of the abutment. When the connection arrangement is used at a position in the patient's mouth which is at all times under considerable loading, material fatigue could come about after a period of time and could result in a fracture at this weak point. In addition, the lateral bore has to be sealed off provisionally, in preparation for the impression-taking, and then opened again. This entails additional work.

The aforementioned implants 1 are known per se (cf. SCHROEDER, SUTTER, BUSER, KREKELER, ibid.).

Such an implant 1 has at the top the implant head 10 and at the bottom the shaft portion 20, the implant head 10 ending at the very top with the radially encircling implant shoulder 11, and it being possible for an external thread 23 to be present on the shaft portion 20 depending on the implant type. The implant shoulder 11 surrounds the opening of the receiving bore 12 which conically narrows axially downwards, as a result of which the inner cone 14 is created. At the bottom 13 of the bore, the receiving bore 12 merges into a coaxial threaded bore 21 which is of reduced diameter and which extends into the shaft portion 20. The internally threaded bore 21 presents the internal thread 22.

In the abovementioned connections made up of implant and abutment, there is the additional problem of rotationally securing the abutment fitted in the implant and the problem of the height tolerance of the head part of the abutment protruding above the implant shoulder. Depending on the depth of insertion of the abutment, a position tolerance is added to the length tolerance of the abutment, so that the head part of the abutment protrudes to a greater or lesser extent above the implant shoulder. When manufacturing the implantology components, the overall resulting height tolerance demands a high and costly level of precision and yet, during further procedures, i.e. on impression-taking, on producing the master model, and on creating the artificial tooth crown, necessitates a high outlay, with, in the final analysis, disturbing tolerances still occurring.

To overcome the disadvantages which to this extent still exist, various constructional solutions have been proposed. The rotational securing of the abutment, which can be fitted into the implant or can be placed on the implant, has been guaranteed by providing at the very bottom of the abutments a non-rotationally symmetrical contour which comes into engagement with a complementary contour present on the implant head. The implant heads in most cases have an inner receiving contour, while the abutments have an outer counter-contour which can be fitted into the receiving contour (cf. U.S. Pat. Nos. 4,713,003, 5,000,686, 5,022,860, 5,030,095, 5,195,892 and 5,281,140 and also EP 0 504 119). JP 95-28877 B2 may be mentioned as an example of the reversal of positive locking with an implant head on which there is an outer contour which is complementary to an inner contour arranged on the abutment. However, none of the implants mentioned above is of the type with a conical, axial receiving bore; at best, the implant shoulder has a conical geometry.

CA 1 313 597 discloses a multi-component implant arrangement with an implant, an intermediate piece which can be placed thereon, and an abutment which can be screwed through the intermediate piece and into the implant. An internally threaded bore is provided in the implant head, and the intermediate piece has a conical through-bore into which the conical root portion of the abutment can be fitted. Contours complementary to one another and providing for rotational securing are arranged on the implant head and on the intermediate piece. Here, once again, the implant does not have a conical, axially extending receiving bore. The abutment itself is rotationally secured only to a limited extent by the threaded segment which is to be screwed into the implant head.

An implant with an inner polygon on the inner cone is proposed by WISKOTT, H. W. A. and BELSER, U. C.: Mechanical resistance of cemented post and core buildups for ITI-Bonefit implants. Clinical Oral Implantology Research, 1992, H.3, page 128 et seq. The inner polygon is provided directly at the transition to the internal thread. The associated abutment has an outer polygon which adjoins the root portion at the bottom and which complements the inner polygon, and from which outer polygon an anchoring pin extends further downwards. The abutment is fitted into the implant so that the outer polygon of the former sits with positive locking in the inner polygon of the implant. For axially fixing the abutment in the implant, the anchoring pin protruding into the internal thread of the implant is cemented in place. This solution is thus restricted to the cementing or bonding of an anchoring pin in the internal thread of the implant.

WO-A-94 09717 discloses a largely similar configuration as regards the inner polygon in the implant and the outer polygon on the abutment. The inner polygon is once again located at the transition to the internal thread; the outer polygon is correspondingly provided on the abutment.

Object of the invention

Given that the functional reliability of the hitherto disclosed connection arrangements is not wholly satisfactory, and that this fact can be attributed to constructional features, the invention is based on the following problem. A connection arrangement between an implant and a straight or angled abutment is to be created which possesses highly reliable stability. In addition, it must be possible for the abutment to be fixed securely and in a practical manner on the implant, and it should not come loose as a result of microscopic movements. What is more, the connection arrangement should consist of the fewest possible simple components and thus should be able to be manufactured inexpensively. Finally, it is desirable that at least some parts of the connection arrangement should have system design features and can therefore be used for different variants of the connection arrangement, i.e. for the combination with different abutments.

Moreover, no wholly satisfactory constructional solution has as yet been made known for an implant with a non-rotationally symmetrical receiving contour on the inner cone and an associated, complementary abutment of the type in question here, which can be joined together using a connection arrangement. The invention thus has at the same time the object of perfecting the implants of the generic type and the complementary abutments, which can be held together by the associated connection arrangement. The abutment, which is fitted into the implant via its conical root portion in a manner as free as possible from clearance, has to be rotationally secured and must not exhibit any axial instability whatsoever. The implant and abutment should be able to be screwed together so that the insertion of the abutment into the implant can be carried out without adhesive binder and so that the connection can be undone again, if need be. For special applications, it is desirable also to be able to fit into the implant abutments which are conventional and have a conical root portion, i.e. with a threaded plug arranged at the very bottom, but without a non-rotationally symmetrical outer counter-contour.

Finally, a screwdriver for establishing the connection between an implant and a straight or an angled abutment is to be developed. With this screwdriver, it should also be possible for screwing to be carried out at an angle.

Nature of the invention

The principle of the proposed connection arrangement between an implant and an abutment consists in the abutment being provided with an inlet, which could be a continuous axial passage. A clamping screw can be fitted head first into this inlet via the root portion, its threaded segment, reduced in diameter compared to the head, being intended to engage in the axially extending internally threaded bore in the implant. Before the clamping screw is fitted into the abutment, an expanding ring is pushed onto the shank segment of the clamping screw, this segment lying between the head and the threaded segment. The expanding ring snaps into a groove arranged in the inlet of the abutment. For partially receiving the expanding ring on the clamping screw, a radial groove is provided underneath the head.

It has proven expedient to give the expanding ring a slotted configuration. In the head of the clamping screw there is a non-rotationally symmetrical recess which serves for engagement of an insertion tool. When tightening or unscrewing the clamping screw, the insertion tool is passed through the continuous axial passage into the recess in the screw head. In the case of angled abutments, it is expedient to provide, in addition to the likewise angled and continuous inlet, a lateral opening for the insertion tool to pass through. Such a lateral opening is arranged in particular in cases where the inlet is not continuous. In the interest of the system design nature of all the implant elements, it is of advantage if the internally threaded bore in the implant and the internally threaded section in the abutment, as well as the threaded segment of the clamping screw, have dimensions which are similar or complementary.

The characterizing feature of the implant according to the invention is that a non-rotationally symmetrical receiving contour is provided in the inner wall of the conical receiving bore, i.e. on the inner cone of the implant head, with a radially uninterrupted section of the inner cone in each case remaining both above the receiving contour and also below it. If a polygon is provided as the receiving contour, then this is designed solidly on the underside, while its points run out towards the top in a parabola shape.

The essential features of the abutment according to the invention are the following: In the case of a continuous inlet, an internally threaded section can be provided at the top, into which section it is possible to insert an occlusal screw for the purpose of fixing the superstructure to be arranged thereon. An outer counter-contour complementary to the receiving contour is provided on the root portion of the abutment and can be designed especially and advantageously as an outer polygon. In analogy to the positioning of the receiving contour present in the implant, the counter-contour is arranged such that a radially uninterrupted segment of the root portion remains both above it and below it, and the circumferential surfaces of both segments are flush with one another. However, the lower segment can also be omitted. In the inlet, inside the area of the root portion, there is a radially encircling groove.

Through the inlet provided in the abutment, if this inlet is continuous, or, if not, through the additional lateral opening, it is possible for a special screwdriver to be engaged with positive locking in the complementary recess in the head of the clamping screw even at an angle. The screwdriver head is multi-edged and presents, in vertical cross-section, a pear-shaped configuration.

By virtue of the invention, a connection arrangement, an implant and a complementary abutment are now available which are distinguished by advantageous assembling and dismantling. Furthermore, the stable and precise holding in the assembled state is guaranteed to be highly reliable. Both straight and angled abutments of the type according to the invention, and conventional straight abutments, can be fitted into the implant modified in accordance with the invention. That is to say, abutments which have a conical root portion and which do not have a counter-contour can also be fitted into the implant with the special receiving contour in the implant head. These abutments can similarly be fixed using separate clamping screws, or the abutments are in one piece and, in a known manner, have at the very bottom a threaded plug which engages in the internally threaded bore in the implant. The special screwdriver is advantageous for inserting the clamping screw when using an angled abutment without an additional lateral opening, but it can also be used with straight abutments.

DRAWINGS AND ILLUSTRATIVE EMBODIMENT

A number of illustrative embodiments of the connection arrangement according to the invention, of the internal configuration of the implant, of the abutment, and of the special screwdriver, are described in detail hereinbelow, with reference to the attached drawings. Possible modifications are discussed at the end. In the drawings:

FIG. 2A shows a straight abutment in vertical section;

FIG. 2B shows an angled abutment with a lower conical portion;

FIG. 2C shows an angled abutment with radially encircling collar, which sits on the implant shoulder;

FIG. 4A shows a clamping screw with expanding ring applied;

FIG. 4B shows the clamping screw with expanding ring pushed on;

FIG. 4C shows the clamping screw with expanding ring when being pushed into an abutment according to FIG. 2B;

FIG. 4D shows the clamping screw with expanding ring once pushed completely into the abutment according to FIG. 2B;

FIG. 4E shows the complete connection arrangement according to FIG. 2B between implant and abutment, with special screwdriver standing by;

FIG. 6B shows the abutment according to FIG. 6A in vertical partial section;

FIG. 6C shows the abutment according to FIG. 6A with inserted clamping screw and expanding ring in vertical partial section;

FIG. 7A shows the implant according to FIG. 5 with inserted abutment according to FIG. 6A;

FIG. 7B shows an enlarged representation from FIG. 7A;

FIG. 7C shows the representation according to FIG. 7A with the abutment likewise in partial section;

FIG. 1B

Figure 1A:
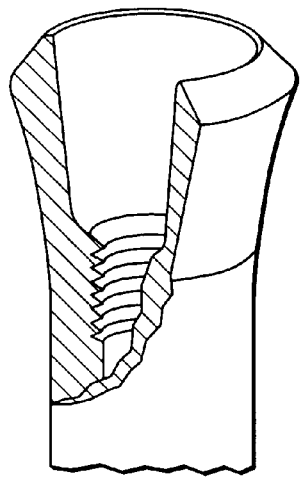
FIG. 1A shows an implant according to the prior art in partial section.
Figure 1B:
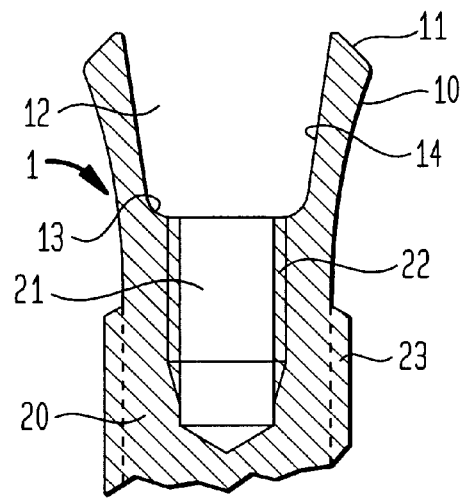
FIG. 1B shows the implant according to FIG. 1A in vertical section.
Figure 1C:
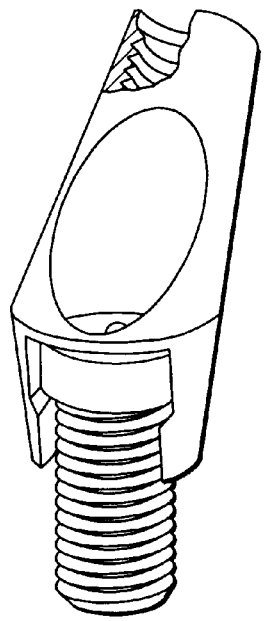
FIG. 1C shows an angled abutment, with inserted clamping screw according to the prior art.
Figure 1D:
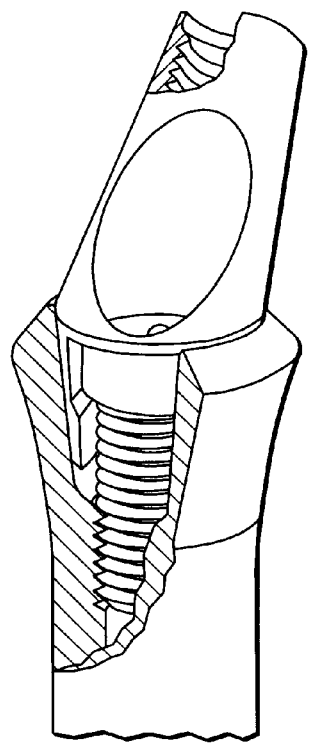
FIG. 1D shows the structural components according to FIGS. 1A to 1C screwed together.

The implant 1 used in the connection arrangement constitutes the basic element thereof and has a structure which is known per se. The upper portion, which is shown alone here, could belong both to a hollow screw implant as well as to a solid screw implant. The connection arrangement is, however, equally suitable for hollow-body implants and solid-body implants in the straight or angled version. For a further description of the implant 1, reference is made to the description of FIGS. 1A to 1D in the Prior Art section.

The following statement holds true for the whole of the description which follows. If, for the sake of the clarity of the drawings, reference numbers are included in a Figure, but are not explained in the immediately relevant text of the description, then reference is made to their mention in the preceding Figure descriptions. In the interests of intelligibility, repeated designation of structural parts in succeeding Figures is in most cases dispensed with, as long as it can clearly be discerned from the drawings that "recurring" structural parts are concerned.

FIG. 2A

The straight abutment 100 has an upper neck portion 110 tapering conically towards the top, and a lower root portion 120 tapering conically towards the bottom. Extending axially through the abutment 100 is an inlet 130 which at the very top opens out in a screw seat 131. Adjoining the screw seat 131 there is a downwardly extending internally threaded section 132 which ends before the transition 140 between the neck portion 110 and the root portion 120. The internally threaded section 132 merges at a bevelled surface 133 into a widened screwhead section 134. The inlet 130 opens out at the end 121 of the root portion 120, the end 121 having a rounded contour 122, and, before the rounded contour 122 is reached, a radially encircling, band-shaped groove 135 is provided and serves to receive an expanding ring.

FIG. 2B

The straight, rotationally symmetrical abutment 100 is almost identical in construction to the angled abutment 200 shown here. The angled abutment 200 also has a neck portion 210 which tapers conically towards the top and which merges at the transition 240 into a root portion 220 tapering conically towards the bottom. However, the neck portion 210 and the root portion 220 are not arranged coaxial to one another, but are instead set at an angle to one another at the transition 240, with the result that the inlet 230 extending through the abutment 200 is also appropriately angled. At the very top, the inlet 230 likewise opens out in a screw seat 231, which is adjoined by an internally threaded section 232 extending downwards. At an asymmetrical bevelled surface 233, the internally threaded section 232 merges into a widened screwhead section 234. The inlet 230 opens out in the root portion 220 at the end 221, which has a rounded contour 222. Here too, before the mouth is reached, a radially encircling groove 235 is provided in the inlet 230.

FIG. 2C

The modified angled abutment 300 differs markedly from the abutment 200. The neck portion 310 is still approximately identical, whereas the root portion 320 shows considerable changes. The transition 340 is also of different design. An angled inlet 330 once again extends through the abutment 300. The neck portion 310 also tapers conically towards the top, and the root portion 320 is set at an angle to the neck portion at the transition 340. Here too, the inlet 330 opens out in a screw seat 331, which is adjoined by an internally threaded section 332 which extends downwards and which merges into a widened screwhead section 334 via an asymmetric bevelled surface 333. The inlet 330 opens out in the root portion 320 with the rounded contour 322 at the end 321. In the shortened root portion 320, i.e. between the transition 340 and the rounded contour 322 terminating at the bottom, the inlet 330 is once again provided with a radially encircling, band-shaped groove 335. The transition 340 acquires its particular configuration by virtue of the fact that a recess 341 is present on the underside of the neck portion 310, and the neck portion 310 continues in the form of a downwardly widening collar 342. This collar 342 forms an annular counter-shoulder 343 which, upon assembly with the implant 1, sits on the inner ring part of the implant shoulder 11 (see FIG. 1B).

FIG. 2D

Figure 2D:
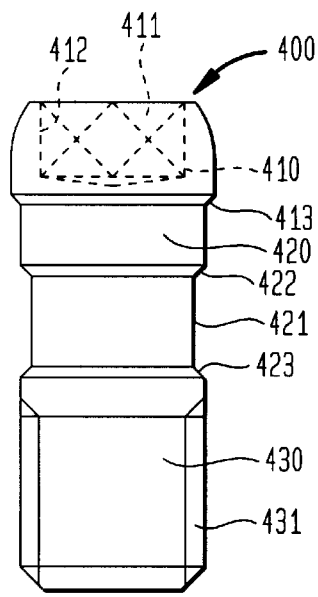
FIG. 2D shows a clamping screw.
Figure 2E:
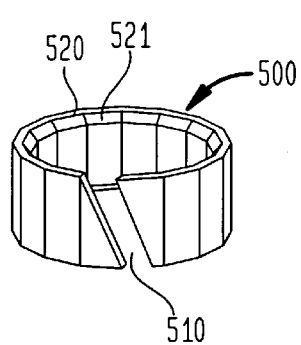
FIG. 2E shows an expanding ring.

For constructing the connection arrangement according to the invention on the implant 1, one of the above-described abutments 100, 200, 300 is alternately necessary; a clamping screw 400 is needed for each of the different connection arrangements. The clamping screw 400 comprises—from the top downwards—the head 410, the adjoining shank segment 420 of reduced diameter, and the lower threaded segment 430. On the upper side of the head 410 there is a recess 411 with an inner contour 412 which is designed to be complementary to the screwdriver head (see FIGS. 4E and 8A to 8E). A bevelled bearing surface 413 forms the transition between the head 410 and the shank segment 420. Approximately in the middle, the shank segment 420 has a radially encircling groove 421 for partial, temporary inclusion of an expanding ring (see FIG. 2E). Bevels 422 and 423 form the respective transitions from the groove 421 to the full diameter of the shank segment 420. The threaded segment 430 has the external thread 431 and is designed complementary to the threaded bore 21 in the implant 1, so that the threaded segment 430 can be screwed into the threaded bore 21.

FIG. 2E

The tire-like expanding ring 500 has a slot 510 forming an opening in it. It has proven advantageous to arrange the slot 510 obliquely and sloping upwards towards the left. The top edge 520 of the expanding ring 500 has an inwardly directed bevelled surface 521 which is designed complementary to the bearing surface 413 on the head 410 of the clamping screw 400. The dimensions of the expanding ring 500 are chosen such that it can be pushed onto the clamping screw 400 and snap into the groove 421 of the latter.

Figure 2F:
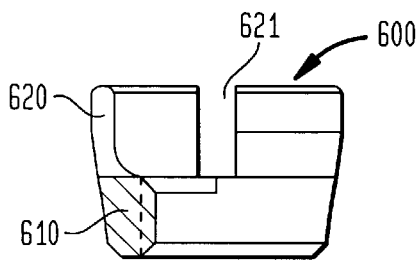
FIG. 2F shows a centering sleeve in a front view.
Figure 2G:
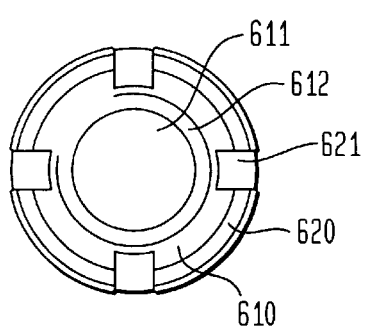
FIG. 2G shows the centering sleeve according to FIG. 2F in plan view.

FIGS. 2F and 2G

When constructing a connection arrangement with an angled abutment 300, a centering sleeve 600 which is in principle rotationally symmetrical is additionally inserted. The centering sleeve 600 consists of a tire-like base portion 610 and an adjoining circumferential continuation 620 extending upwards. Outwardly, the centering sleeve 600 widens conically towards the top. In the base portion 610 there is an axial bore 611 with an internal thread 612, so that the centering sleeve 600 can be screwed onto the threaded segment 430 of the clamping screw 400. The circumferential continuation 620 has a thinner wall than the base portion 610, as a result of which the clearance in the interior of the centering sleeve 600 is increased. A number of vertical expansion slots 621 are provided within the circumferential continuation 620 and extend approximately to the level of the base portion 610.

FIG. 3A

A straight abutment 100 is fixed on an implant 1 by means of the clamping screw 400 and the expanding ring 500, the conical root portion 120 of the abutment 100 engaging in the main bore 12, i.e. in the inner cone 14, of the implant 1. The head 410 of the clamping screw 400 sits in the screwhead section 134 inside the inlet 130, and the expanding ring 500 applied on the clamping screw 400 lies with its bevelled surface 521 on the bearing surface 413 of the clamping screw 400. At the same time, the expanding ring 500 is set in the groove 135 of the abutment 100. The threaded segment 430 of the clamping screw 400 is screwed tightly into the threaded bore 21 of the implant 1; the external thread 431 and the internal thread 21 are in engagement with one another. By means of the tensile force of the clamping screw 400 transmitted to the expanding ring 500, the abutment 100 is fixed securely both axially and also against rotation. The conicity of the root portion 120 and of the inner cone 14 affords reliable stability of the connection arrangement. The internally threaded section 132 is used for fixing additional buildups.

FIG. 3B

Figure 3A:
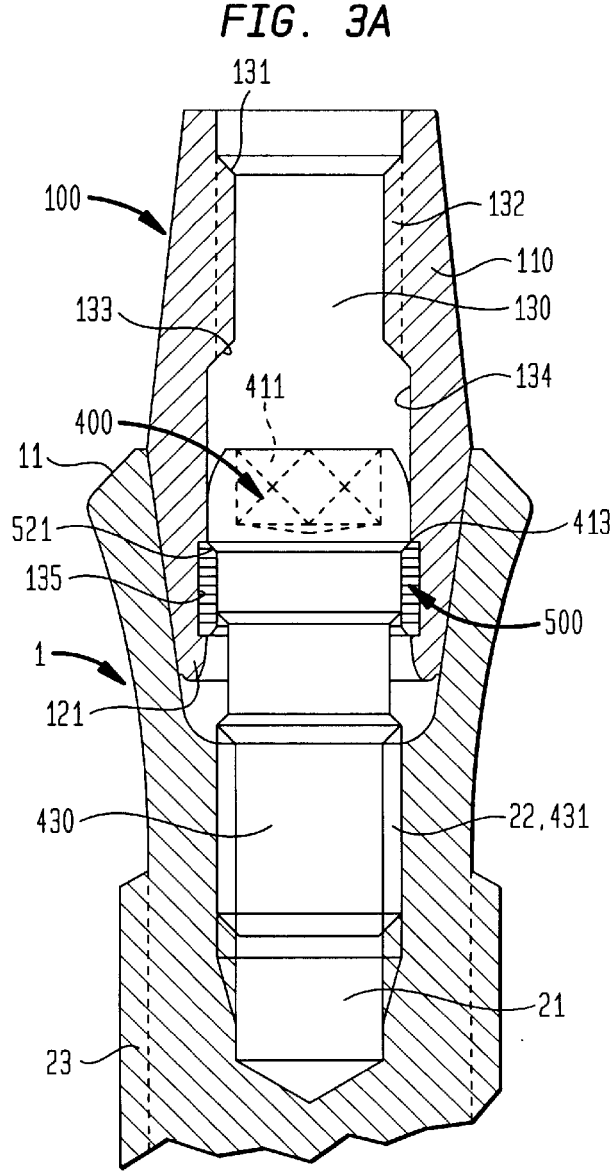
FIG. 3A shows a connection arrangement between an implant and the straight abutment according to FIG. 2A.
Figure 3B:
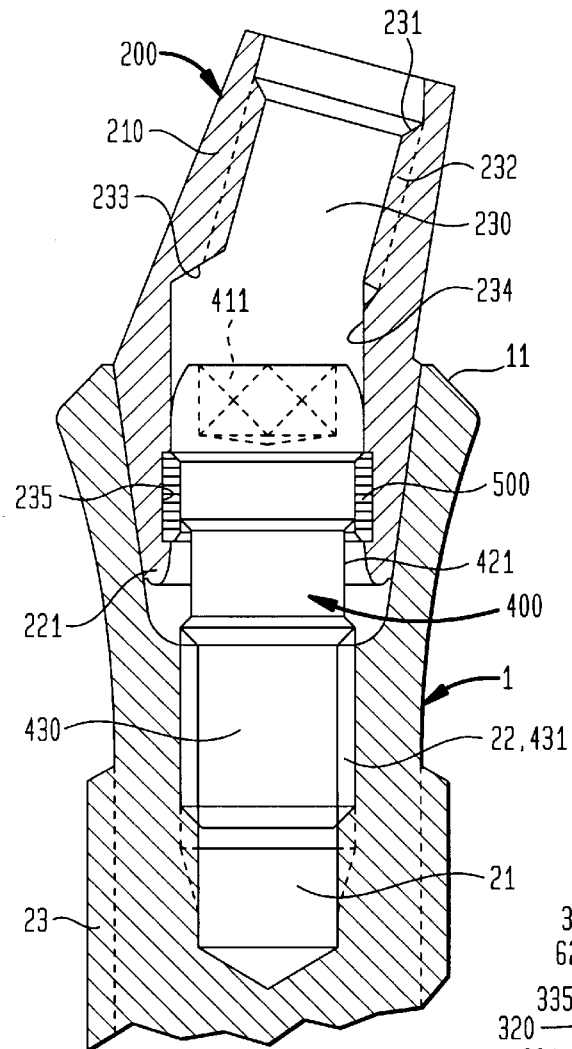
FIG. 3B shows a connection arrangement between an implant and the angled abutment according to FIG. 2B.
Figure 3C:
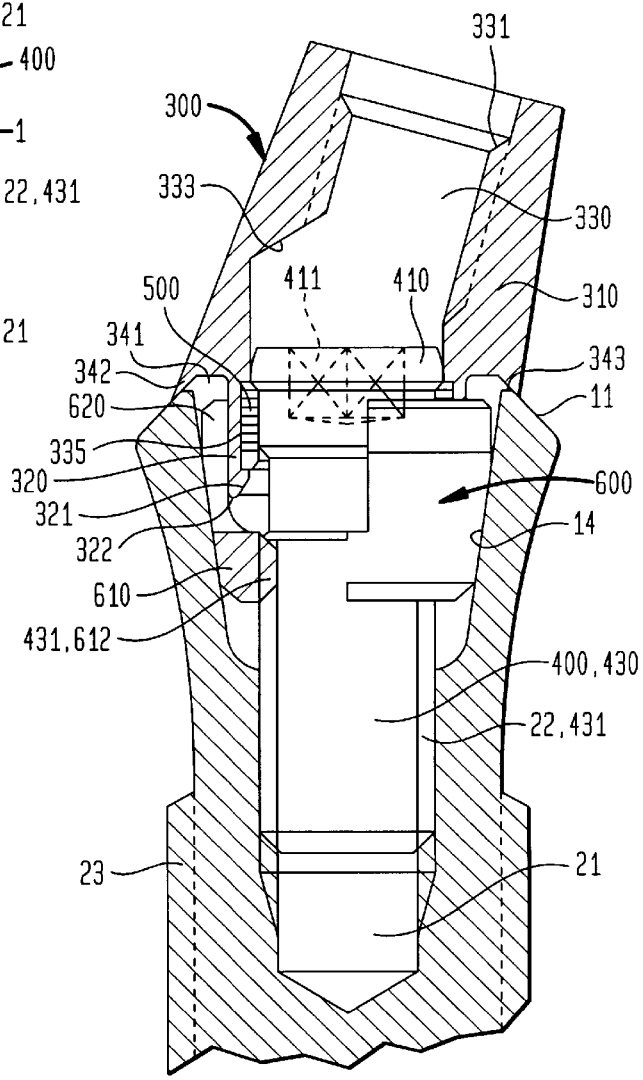
FIG. 3C shows a connection arrangement between an implant and the angled abutment according to FIG. 2C.
Figure 5:
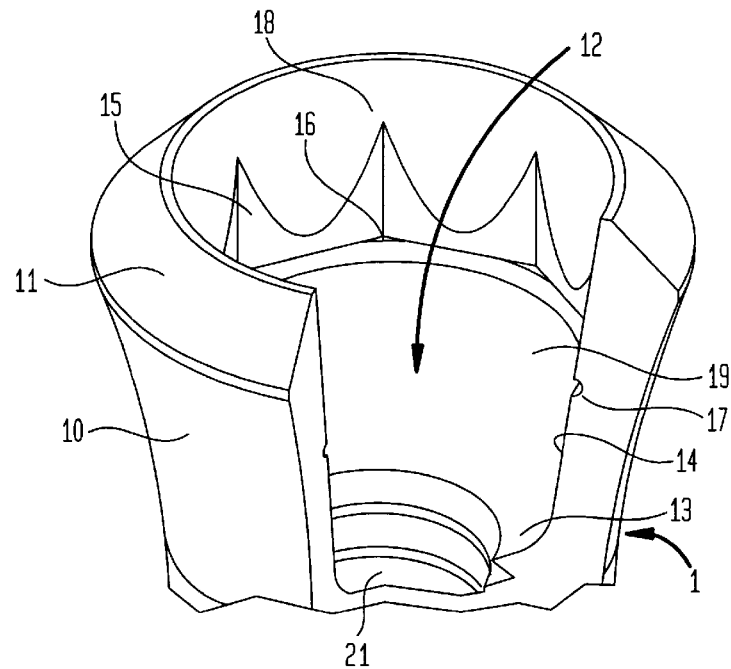
FIG. 5 shows an implant head with the receiving contour in partial section.
Figure 6A:
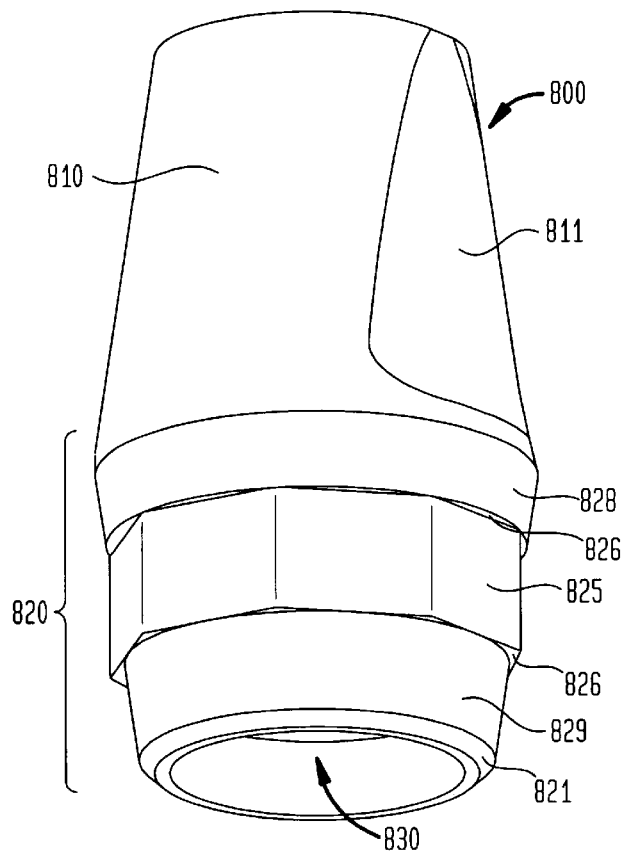
FIG. 6A shows a perspective view of an abutment with a counter-contour on the conical root portion and a securing surface on the head part.

Here, an angled abutment 200 is fixed on an implant 1 by means of the clamping screw 400 and the expanding ring 500. The structural parts are connected to one another in an analogous manner to that depicted in FIG. 3A.

FIG. 3C

An angled abutment 300 is fixed on the implant 1, its counter-shoulder 343, formed by the collar 342, being supported on the inner ring surface on the implant shoulder 11. In this connection arrangement too, the clamping screw 400 and the expanding ring 500 hold it together and ensure its permanent stability in the chosen positioning, the centering sleeve 600 additionally being inserted. The centering sleeve 600 has been screwed onto the threaded segment 430 of the clamping screw 400 inside the main bore 12 of the implant 1 and bears snugly on the inner cone 14 thereof. The external thread 431 of the clamping screw 400 and the internal thread 612 of the centring sleeve 600 are in engagement with one another. The expanding ring 500 lies in the groove 335 of the root portion 320 of the abutment 300, the end 321 with the rounded contour 322 engaging under the expanding ring 500. The circumferential continuation 620 of the centering sleeve 600 is clamped between the root portion 320 of the abutment 300 and the inner cone 14 of the implant 1. Here too, the head 410 of the clamping screw 400 sits so closely on the expanding ring 500 that the bearing surface 413 and the bevelled surface 521 are pressed against one another.

FIGS. 4A to 4E

The production of the connection arrangement is now described with reference to this sequence of Figures, using by way of example an angled abutment 200.

FIG. 4A

The expanding ring 500 is pushed onto the clamping screw 400 via the threaded segment 430 and first surrounds the external thread 431. In this way, the sufficiently elastically deformable expanding ring 500 bends open, i.e. the slot 510 enlarges.

FIG. 4B

The expanding ring 500 is pushed further in the axial direction onto the clamping screw 400, until the groove 421 on the shank segment 420 is reached, at which point the expanding ring 500 positions itself as a consequence of its inherent stress. Since the groove 421 has a smaller diameter than the threaded segment 430, which has been crossed beforehand, and the lower section of the shank segment 420, the expanding ring 500 can contract slightly, as a result of which the slot 510 narrows.

FIG. 4C

Pre-assembled thus far, in the next step the clamping screw 400 with the pushed-on expanding ring 500 is pushed from below into the abutment 200, i.e. via the end 221 into the inlet 230. The rounded contour 222 at the end 221, and the existing play of the expanding ring 500 sitting in the groove 421, permit smooth insertion of the combination of clamping screw 400 and expanding ring 500 into the abutment 200. The head 410 of the clamping screw 400 thus passes gradually into the screwhead section 234.

FIG. 4D

After continued axial pushing, the head 410 approaches the bevelled surface 233 in the abutment 200 and at the same time the expanding ring 500 reaches the groove 235, into which the expanding ring 500 snaps on account of its prestressing. Here, the expanding ring 500 can expand outwards again, as a result of which the slot 510 enlarges again.

FIG. 4E

Finally, the abutment 200 is fitted into the implant 1 in the desired position of rotation. The clamping screw 400 is now screwed tight using a special screwdriver 700 passing through the neck portion 210 and the inlet 230. The screwdriver head 710 engages with its outer contour 711, which is complementary to the inner contour 412 of the clamping screw 400. The threaded segment 430 of the clamping screw 400 is screwed gradually into the threaded bore 21 present in the implant 1, and at the same time the upper, cylindrical section of the shank segment 420 is thus screwed into the positioned expanding ring 500. This screwing-in is promoted by the bevel 422. The slotted expanding ring 500 widens and is positioned in the groove 421 with remaining play. When the clamping screw 400 is tightened further, a rigid and secure connection is obtained between the implant 1 and the fitted abutment 200.

The same operational steps are required if a connection arrangement with a straight abutment 100 or an angled abutment 300 is to be constructed. When using the special, angled abutment 300, the centering sleeve 600 has to be screwed onto the clamping screw 400 before fitting the combination of clamping screw 400 and expanding ring 500 into the implant 1.

FIG. 5

The implant 1 used in the connection arrangement constitutes the basic element thereof and has a structure known per se, except for the special non-rotationally symmetrical receiving contour 15 in the inner cone 14 in the implant head 10. Here, the receiving contour 15 is designed as a radially encircling polygon. This polygon can be created by removal of material, for which purpose a radially encircling groove 17 underneath the receiving contour 15, and likewise in the inner cone 14, is recommended for the machining. By means of the removal of material, steps 16 are created at the bottom of the polygon. On the underside, the polygon is of solid design, whereas it runs out in parabolic points towards the top. The receiving contour 15 advantageously lies in the inner cone 14 in such a way that uninterrupted sections 18, 19 of the inner cone 14 remain, both above the receiving contour 15 and also under it. For as stable and tight a fit as possible of the abutment which is to be inserted, it is advisable to design the upper section 18 with sufficient height.

FIG. 6A

The abutment 800 has the neck portion 810 at the top, and the cone portion 820 adjoining it at the bottom. The inlet 830, here in the form of a continuous axial passage, extends through the abutment 800. By way of example, at least one plane surface 811, in principle running vertically, is provided on the neck portion 810 and serves to rotationally secure the crown cap or superstructure which is to be arranged at a later stage on the abutment 800. At the same time, the plane surface 811 can be used for applying a screwing-in tool. It is an advantageous alternative to provide three plane surfaces 811 each offset by 1200. The plane surface 811 runs out in an arcuate shape in the direction of the cone portion 820.

The cone portion 820 has a counter-contour 825 which is complementary to the receiving contour 15 present in the implant 1, so that the abutment 800 can be fitted, rotationally secured, into the implant 1. Analogous to the recessed polygon designed as the receiving contour 15, the counter-contour 825 is likewise designed as a polygon in this example. The counter-contour 825 is arranged on the cone portion 820 in such a way that, in this case too, uninterrupted segments 828, 829 of the cone portion 820 remain. The circumferential surfaces of both segments 828, 829 are flush with one another, in the same way as the sections 18, 19 of the inner cone 14 in the implant head 10 are also flush with one another. Steps 826 are produced at the transitions from the segment 828 to the counter-contour 825, and from the latter to the segment 829. At the very bottom, the abutment 800 and its segment 829 terminate at the end 821. It is also possible to arrange the counter-contour 825 immediately adjoining the end 821.

FIG. 6B

Within the inlet 830, an internally threaded section 832 can be provided beginning at the top, and before the lower opening of the inlet 830 there is a radially encircling groove 835. The possible internally threaded section 832 would serve to receive an occlusal screw with which the superstructure could be fastened on. The threaded pin of the occlusal screw extends only partially into the inlet 830. An unthreaded screwhead section 834 remains between the internally threaded section 832 and the groove 835.

FIG. 6C

For constructing the connection arrangement consisting of implant 1 and abutment 800, a clamping screw 400 is used. The clamping screw 400 comprises—from the top downwards the head 410, the adjoining shank segment 420 of reduced diameter, and the lower threaded segment 430. On the upper side of the head 410 there is a recess 411 with an inner contour 412 which is designed to be complementary to the tip of the insertion tool used. Underneath the head 410, the shank segment 420 is provided with a radially encircling groove 421 for partial inclusion of the expanding ring 500. The threaded segment 430 is designed complementary to the internally threaded bore 21 in the implant 1, so that the threaded segment 430 can be screwed into the internally threaded bore 21.

The clamping screw 400 with the expanding ring 500, which sits in the groove 421, is pushed into the inlet 830 of the abutment 800 from below, and with the head 410 leading, until the expanding ring 500—this could be tyre-shaped and slotted—snaps into the groove 835 present in the abutment 800. The head 410 of the clamping screw 400 thus comes to lie inside the screwhead section 834 in the inlet 830 of the abutment 800. The insertion tool can be guided in through the inlet 830 to the head 410 of the clamping screw 400.

FIGS. 7A to 7C

In the assembled state, the abutment 800—here provided with a plane surface 811—sits with its conical root portion 820 in the implant head 10, while the neck portion 810 of the abutment 800 protrudes above the implant shoulder 11. The sections 18, 19 of the inner cone 14 come to lie against the segments 828, 829 of the root portion 820 of the abutment 800. The counter-contour 825 of the abutment 800 sits in the receiving contour 15 of the implant 1. The tightened clamping screw 400 presses via its head 410 on the expanding ring 500, which also sits partially in the groove 835 in the abutment 800. The threaded segment 430 of the clamping screw 400 engages in the internally threaded bore 21 in the implant 1. The abutment 800 is in this way drawn into the implant 1, guaranteeing axial fixing and rotational securing. At the level between the receiving contour 15 and the counter-contour 825 there is a certain play, so that the step 826 of the counter-contour 825 under no circumstances sits on the step 16 in the implant 1. The important factor is that the conical surfaces 18, 19; 828, 829 of both parts 1, 800 lie against one another.

FIG. 8A

The head 410 of the clamping screw 400 has, on its upper side, the recess 411 extending axially down and with the four-edged inner contour 412. In each of the corner areas, the inner contour 412, which in principle is square in horizontal cross-section, has a positive, inwardly directed chamfer 414.

Figure 8A:
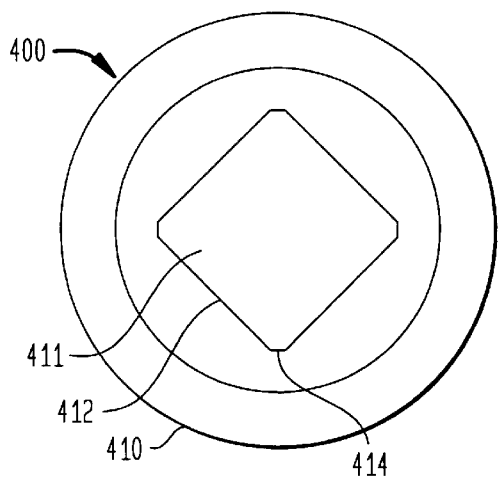
FIG. 8A shows the plan view of the head of the clamping screw according to FIG. 2D.
Figure 8B:
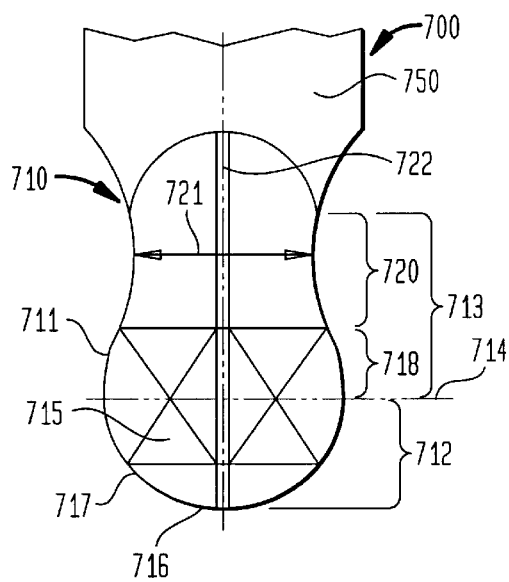
FIG. 8B shows the screwdriver head in front view.
Figure 8C:
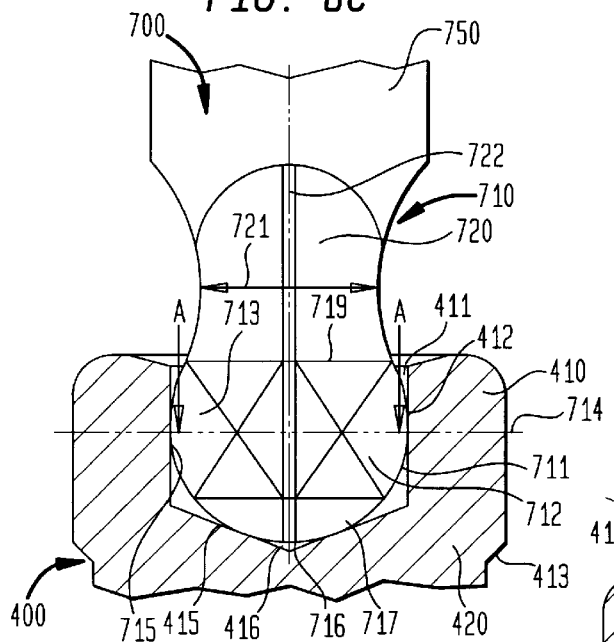
FIG. 8C shows the perpendicular engagement of the screwdriver head into the recess provided in the head of the clamping screw.
Figure 8E:
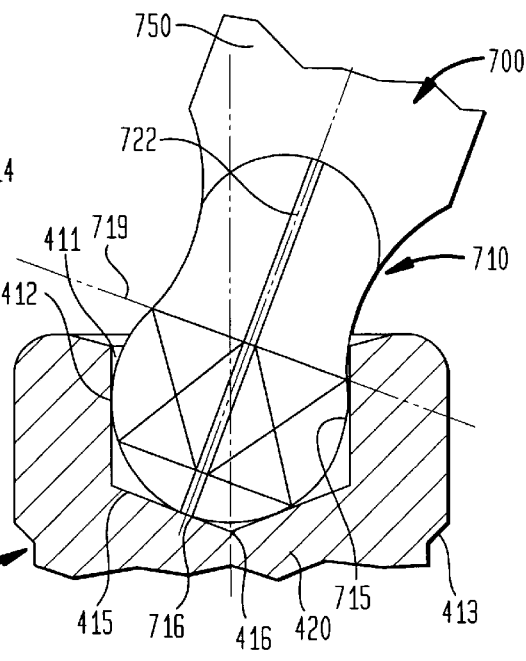
FIG. 8E shows the angled engagement according to FIG. 8C.
Figure 8D:
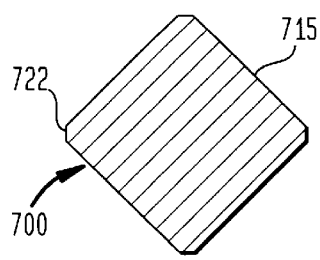
FIG. 8D shows the horizontal section A—A through the screwdriver head.

FIGS. 8B to 8D

The screwdriver head 710 has an outer contour 711 which can fit in the recess 411, having the inner contour 412, and which is divided into a lower hemispherical section 712 and an upper waist section 713 which are joined to one another at the section transition 714—at this point the screwdriver head 710 has the greatest cross-width. At the horizontal section transition 714 the screwdriver head 710 has in principle a square cross-section with chamfers 722 in the corner areas; outwardly, this therefore gives a square 715. The essentially four-edged outer contour 711 of the screwdriver head 710 engages with positive locking in the essentially four-edged inner contour 412 in the head 410 of the clamping screw 400. Viewed in horizontal cross-section, the quadrate formed by the square 715 merges gradually into a circular surface in the direction towards the screwdriver tip 716, i.e. outwardly, the square 715 harmoniously becomes a spherical dome 717.

The waist section 713 starting at the section transition 714 has, when viewed in vertical section, firstly the configuration of an upwardly tapering spherical disc 718 which, at the boundary line 719, merges into an attachment piece 720 narrowed in a hyperbola shape, widens out again from the narrowest waist line 721, and finally adjoins the rod section 750 of the special screwdriver 700. Viewed in horizontal cross-section, the square 715 extends across the section transition 714 upwards in the direction of the waist section 713 approximately to the boundary line 719 and here once again runs out in a harmonious manner, so that the quadrate formed by the square 715 merges gradually into a circular surface towards the attachment piece 720.

It is of advantage, from the point of view of production engineering and function, if the blind recess 411 in the head 410 of the clamping screw 400 opens out at the bottom 415 into a wide-angled cone tip 416 which reaches almost to the level of the bearing surface 413 forming the transition to the upper shank segment 420. If a straight abutment 100 is being fixed in an implant 1 by means of the clamping screw 400, then, during the screwing procedure, the special screwdriver 700 engages with its rod section 750 through the inlet 130 and with its screwdriver head 710 vertically into the recess 411. The square 715 of the special screwdriver 700 engages with positive locking in the four-edged inner contour 412 of the clamping screw 400, the screwdriver tip 716 sits on the bottom 415 or comes close to the latter, and the boundary line 719 coincides approximately with the top edge of the clamping screw 400.

FIG. 8E

If an angled abutment 200 or 300 is being fixed in an implant 1 by means of the clamping screw 400, then, during the screwing procedure, the special screwdriver 700 engages with its rod section 750 through the oblique inlet 230 or 330, and with its screwdriver head 710, consequently also obliquely, into the recess 411 of the head 410 of the clamping screw 400. The square 715 is now applied at an angle, but still with positive locking, in the four-edged inner contour 412 of the clamping screw 400; the screwdriver tip 716 is positioned eccentrically with respect to the bottom 415. The boundary line 719, set at an angle to the horizontal, at one end drops into the recess 411 and at the other end protrudes obliquely from the said recess.

In both the straight and the oblique screwing procedures, there must be play available between the inner contour 412 and the outer contour 711, so as to be able to introduce the screwdriver head 710 smoothly into the recess 411 and to withdraw it smoothly therefrom, but also so that, during an oblique screwing procedure, the rotating screwdriver head 710 does not jam and cannot roll elliptically with friction on the inner wall of the recess 411.

Further constructional variations of the above-described illustrative embodiments are possible. The following are mentioned here in particular:

It is also possible, in angled abutments 200, 300, 800 with or without counter-contour 825, to provide a lateral opening for the engagement of a screwdriver for acting on the clamping screw 400. If the inlet 230, 330, 830 is continuous and has an internally threaded section 232, 332, 832 at the top, then the inlet and the thread alone have the function of receiving the occlusal screw for fixing the superstructure. If the inlet 230, 330, 830 is not continuous and there is no internally threaded section 232, 332, 832, then the superstructure is cemented on in the conventional manner.

Instead of being recessed by means of removal of material, the non-rotationally symmetrical receiving contour 15 provided in the inner cone 14 in the implant head 10 could also be raised, in which case there would then have to be a correspondingly recessed counter-contour in the abutment.

As regards the receiving contour 15 and the complementary counter-contour 825, it is possible to use all practicable, non-rotationally symmetrical geometries, such as polygons, ovals, star shapes and rosette shapes, or else simple wedges, pins and journals with their respective complementary, positive-locking formations.

It is also possible for the internally threaded section 132, 232, 332, 832 to be designed with a diameter which is large enough for the clamping screw 400 to be introduced into the abutment 100, 200, 300, 800 from above. If, in this case, a support shoulder for the head 410 of the clamping screw 400 is formed in the abutment 100, 200, 300, 800, then it would be possible to dispense with the groove 135, 235, 335, 835 in the abutment and with the expanding ring 500.

The shape and the presence of outer, rotationally securing contours on the neck portion 810 of the abutment 800 is not obligatory, and the neck portions 810 as such can have any desired, practicable configuration. The plane surfaces 811 could be omitted or replaced by other geometries or formations providing for the rotational securing. On the neck portion 810, an engagement means could be provided for a transverse screwing of the superstructure.

The neck portions 110, 210, 310, 810 of the abutments 100, 200, 300, 800 can be smoothed to the normal extent for adaptation.

The lower conical segment 829 on the abutment 800 can be smaller or larger than the upper segment 828. The segment 829 could also be dispensed with entirely, in which case the counter-contour 825 would extend as far as the end 821.

The abutments 800 can be both straight and angled. In the case of a straight abutment 800 with a continuous inlet 830, the latter extends in a straight line. By contrast, in the case of an angled abutment, whose neck portion is angled in relation to the root portion, a continuous inlet presents a corresponding angled configuration.

As regards the head 410 of the clamping screw 400, instead of the recess 411 with the inner contour 412, it would also be possible to provide an outer contour onto which an insertion tool can be applied.

As regards the clamping screw 400, the lower section of the shank segment 420, which adjoins the threaded segment 430, is not absolutely necessary.

The slot 510 in the expanding ring 500 could also extend approximately vertically; or a plurality of expansion slots could be provided.

The recess 411 in the head 410 of the clamping screw 400 can also be worked without the chamfer 414, so that an exactly four-edged, square inner contour 412 is obtained. The chamfer 722 on the screwdriver head 710 could likewise be dispensed with.

The cone tip 416 sited at the bottom of the recess 411 in the head 410 of the clamping screw 400 is not absolutely necessary for the functioning of the special screwdriver 700.

As an alternative to the four-edged complementary configuration of the recess 411 in the head 410 of the clamping screw 400 and of the outer contour 711 of the screwdriver head 710, it is also possible for both to be provided with five edges.

We claim:

1. In combination:

an implant having a head portion, a shaft portion depending from said head portion, and a bore extending through said head and shaft portions, said bore including an unthreaded section extending through said head portion and an internally threaded section extending through said shaft portion;

an abutment having a neck portion extending outwardly from said bore of said implant and a root portion depending from said neck portion and extending axially into said bore of said implant, said root portion having an axially extending inlet in an end thereof remote from said neck portion and a radially extending groove encircling said inlet and communicating therewith; and connecting means for connecting said abutment to said implant, said connecting means including a clamping screw having a screw head positioned in said inlet of said abutment and an externally threaded segment threadedly engaging said internally threaded section of said bore of said implant, an expanding ring positioned and maintained in said groove of said abutment by said clamping screw, which extends through said ring, and access means, located in said abutment and communicating with said inlet thereof, for permitting access to said screw head by a tool adapted to rotate said clamping screw and thereby thread said externally threaded segment thereof into said internally threaded section of said bore of said implant.

2. The combination of claim 1, wherein said inlet of said abutment is sized and shaped such that said clamping screw can be inserted headfirst into said inlet through said end of said root portion remote from said neck portion.

3. The combination of claim 1 or 2, wherein said clamping screw further includes expanding means for expanding said ring while said ring is positioned in said groove of said abutment.

4. The combination of claim 3, wherein said expanding means includes a shank segment provided on said clamping screw between said screw head and said externally threaded segment, said shank segment being sized and shaped so as to engage said ring and thereby urge it against said abutment, whereby said clamping screw and said ring cooperate to fixedly secure said abutment relative to said implant both axially and rotationally.

5. The combination of claim 4, wherein said shank segment of said clamping screw includes a first section positioned proximate to said screw head, said first section having a first diameter, and a second section positioned between said first section and said externally threaded segment, said second section having a second diameter which is less than said first diameter.

6. The combination of claim 5, wherein said clamping screw is movable axially relative to said abutment from a first position, in which said second section of said shank segment is positioned adjacent said groove of said abutment, to a second position, in which said first section of said shank segment is adjacent said groove of said abutment.

7. The combination of claim 6, wherein said clamping screw is moved from its said first position to its said second position in response to the threading of said clamping screw into said implant.

8. The combination of claim 7, wherein said second diameter is selected such that said second section of said shank segment temporarily receives said ring when said second section is positioned adjacent said groove in said abutment.

9. The combination of claim 8, wherein said first diameter is selected such that said first section of said shank segment engages and expands said ring as said clamping screw is moved from its said first position to its said second position.

10. The combination of claim 9, wherein said clamping screw further includes a first bevelled surface between said screw head and said first section of said shank segment, a second bevelled surface between said first and second sections of said shank segment, and a third bevelled surface between said second section of said shank segment and said externally threaded segment.

11. The combination of claim 10, wherein said first bevelled surface engages said ring when said clamping screw is in its said second position.

12. The combination of claim 11, wherein said ring has a first circular edge located at one end of said ring, a second circular edge located at an opposite end of said ring, and a slot extending completely through said ring between said first and second edges thereof.

13. The combination of claim 12, wherein said first edge of said ring includes a fourth bevelled surface having a shape which is complementary to said first bevelled surface of said clamping screw, said first and fourth bevelled surfaces engaging each other when said clamping screw is in its said second position.

14. The combination of claim 13, wherein said abutment is straight such that said neck and root portions are coaxially aligned, and wherein said inlet extends axially through said root and neck portions of said abutment, the portion of said inlet which extends through said neck portion functioning as said access means.

15. The combination of claim 14, wherein said portion of said inlet which extends through said neck portion of said abutment is internally threaded so as to receive an occlusal screw.

16. The combination of claim 13, wherein said abutment is angled such that said neck and root portions are not coaxially aligned, and wherein said inlet extends axially through said root and neck portions of said abutment, the portion of said inlet which extends through said neck portion functioning as said access means.

17. The combination of claim 16, wherein said portion of said inlet which extends through said neck portion of said abutment is internally threaded so as to receive an occlusal screw.

18. The combination of claim 16, further comprising a centering sleeve positioned in said main bore of said implant, said centering sleeve having an axial bore provided with a non-threaded portion sized and shaped so as to receive said root portion of said abutment and a threaded portion which threadedly engages said externally threaded segment of said clamping screw.

19. The combination of claim 13, wherein said abutment is angled such that said neck and root portions are not coaxially aligned, and wherein said inlet is in the form of a blind hole which communicates with a lateral opening in said abutment, said lateral opening functioning as said access means.

20. The combination of claim 13, wherein said main bore of said implant has a conical contour, and wherein said head portion of said implant is outwardly flared, an end of said head portion remote from said shaft portion being inwardly tapered.

21. The combination of claim 13, wherein said clamping screw further includes a recess in said screw head, said recess having an inner contour which is complementary to a head of a tool adapted to rotate said clamping screw.

22. The combination of claim 21, wherein said recess is in the form of a blind hole extending into said screw head.

23. The combination of claim 1, wherein said ring has a first circular edge located at one end of said ring, a second circular edge located at an opposite end of said ring, and a slot extending completely through said ring between said first and second edges thereof.

24. The combination of claim 23, wherein said ring has a circular sidewall extending between said first and second edges of said ring, and wherein said slot extends completely through said sidewall from a first point on said first edge to a second point on said second edge.

25. The combination of claim 24, wherein said first and second points are circumferentially aligned, whereby said slot is not angled.

26. The combination of claim 24, wherein said first and second points are not circumferentially aligned, whereby said slot is angled.

27. The combination of claim 23, wherein said first edge of said ring has a first bevelled surface.

28. The combination of claim 27, wherein said clamping screw has a second bevelled surface which is complementary to said first bevelled surface, said second bevelled surface being positioned between said screw head and said externally threaded segment of said clamping screw.

29. The combination of claim 1, wherein said groove is located adjacent said end of said root portion remote from said neck portion.

30. An abutment, comprising:
a neck portion;
a root portion depending from said neck portion and having an end remote from said neck portion, said root portion being sized and shaped so as to be insertable into a bore of a mating implant;
an inlet extending longitudinally into said remote end of said root portion;
guiding means located at said remote end of said root portion for guiding a clamping screw into said inlet as it is inserted headfirst through said remote end of said root portion; and
a radially extending groove encircling said inlet and communicating therewith, said groove being positioned between said guiding means and said neck portion and being sized and shaped so as to receive an expanding ring carried by a clamping screw which is being inserted headfirst into said inlet.

31. The abutment of claim 30, wherein said abutment is straight such that said neck and root portions are coaxially aligned, and wherein said inlet extends axially through said root and neck portions of said abutment, the portion of said inlet which extends through said neck portion being sized and shaped such that a tool can be inserted thereinto.

32. The abutment of claim 31, wherein said portion of said inlet which extends through said neck portion of said abutment is internally threaded so as to receive an occlusal screw.

33. The abutment of claim 30, wherein said abutment is angled such that said neck and root portions are not coaxially aligned, and wherein said inlet extends axially through said root and neck portions of said abutment, the portion of said inlet which extends through said neck portion being sized and shaped such that a tool can be inserted thereinto.

34. The abutment of claim 33, wherein said portion of said inlet which extends through said neck portion of said abutment is internally threaded so as to receive an occlusal screw.

35. The abutment of claim 30, wherein said abutment is angled such that said neck and root portions are not coaxially aligned, and wherein said inlet is in the form of a blind hole which communicates with a lateral opening in said abutment, said lateral opening being sized and shaped such that a tool can be inserted thereinto.

36. The abutment of claim 30, wherein said groove is located adjacent said end of said root portion remote from said neck portion.

37. The abutment of claim 30, wherein said neck portion has an outer surface provided with at least one planar section.

38. The abutment of claim 30, wherein said root portion has an outer surface provided with a counter-contour which is complementary to a receiving contour of a mating implant.

39. The abutment of claim 38, wherein said counter-contour has a polygonal shape.

40. The abutment of claim 39, wherein said root portion has a first non-contoured segment positioned adjacent said end of said root portion remote from said neck portion and a second non-contoured segment positioned adjacent an opposite end of said root portion, said counter-contour being positioned between said first and second non-contoured segments.

41. The abutment of claim 40, wherein said first non-contoured segment has an axial length which is greater than that of said second non-contoured segment.

42. The abutment of claim 40, wherein said second non-contoured segment has an axial length which is greater than that of said first non-contoured segment.

43. The abutment of claim 40, wherein said first non-contoured segment is flush with said second non-contoured segment.

44. The abutment of claim 39, wherein at least a portion of said counter-contour is positioned adjacent said end of said root portion remote from said neck portion.

45. The abutment of claim 30, wherein said neck portion includes a screw seat in an end thereof remote from said root portion, a widened screw head section in an opposite end of said neck portion, and an internally threaded section between said screw seat and said screw head section.

46. The abutment of claim 45, wherein said neck portion includes a beveled surface between said internally threaded section and said screw head section.

47. The abutment of claim 45, wherein said screw head section is in communication with said inlet.

48. The abutment of claim 30, further comprising receiving means for receiving a shoulder of a mating implant.

49. The abutment of claim 48, wherein said receiving means is located at the junction of said neck and root portions, said receiving means including a counter-shoulder which is complementary to a shoulder of a mating implant.

50. The abutment of claim 30, wherein said root portion is sized and shaped such that it can be inserted into a centering sleeve.

51. The abutment of claim 30, wherein said guiding means includes a rounded contour at said remote end of said root portion.

52. The abutment of claim 30, wherein said neck portion has a frusto-conical shape and wherein said root portion has a frusto-conical shape.

53. The abutment of claim 30, wherein said neck portion is adapted to mount a dental prosthesis thereon.

54. The abutment of claim 30, wherein said inlet has a length sufficient to receive a head of a clamping screw.

55. An abutment, comprising a neck portion; a root portion depending from said neck portion and being coaxially aligned therewith such that said abutment is straight, said root portion being sized and shaped so as to be insertable into a bore of a mating implant; an inlet extending axially through said root and neck portions, said inlet being sized and shaped such that a clamping screw can be inserted headfirst into said inlet through an end of said root portion remote from said neck portion, the portion of said inlet which extends through said neck portion being sized and shaped such that a tool can be inserted thereinto and being internally threaded so as to receive an occlusal screw; and a radially extending groove encircling said inlet and communicating therewith, said groove being sized and shaped so as to receive an expanding ring.

56. An abutment, comprising a neck portion; a root portion depending from said neck portion such that said neck and root portions are not coaxially aligned, whereby said abutment is angled, said root portion being sized and shaped so as to be insertable into a bore of a mating implant; an inlet extending axially through said root and neck portions, said inlet being sized and shaped such that a clamping screw can be inserted headfirst into said inlet through an end of said root portion remote from said neck portion, the portion of said inlet which extends through said neck portion being sized and shaped such that a tool can be inserted thereinto; and a radially extending groove encircling said inlet and communicating therewith, said groove being sized and shaped so as to receive an expanding ring.

57. The abutment of claim 56, wherein said portion of said inlet which extends through said neck portion of said abutment is internally threaded so as to receive an occlusal screw.

58. An abutment, comprising a neck portion; a root portion depending from said neck portion such that said neck and root portions are not coaxially aligned, whereby said abutment is angled, said root portion being sized and shaped so as to be insertable into a bore of a mating implant; an inlet extending longitudinally into an end of said root portion remote from said neck portion, said inlet being sized and shaped such that a clamping screw can be inserted headfirst into said inlet through said end of said root portion remote from said neck portion, said inlet being in the form of a blind hole which communicates with a lateral opening in said abutment, said lateral opening being sized and shaped such that a tool can be inserted thereinto; and a radially extending groove encircling said inlet and communicating therewith, said groove being sized and shaped so as to receive an expanding ring.

59. An abutment, comprising a neck portion; a root portion depending from said neck portion, said root portion being sized and shaped so as to be insertable into a bore of a mating implant, said root portion having an outer surface provided with a counter-contour of a polygonal shape which is complementary to a receiving contour of a mating implant; an inlet extending longitudinally into an end of said root portion remote from said neck portion, said inlet being sized and shaped such that a clamping screw can be inserted headfirst into said inlet through said end of said root portion remote from said neck portion; and a radially extending groove encircling said inlet and communicating therewith, said groove being sized and shaped so as to receive an expanding ring.

60. The abutment of claim 59, wherein said root portion has a first non-contoured segment positioned adjacent said end of said root portion remote from said neck portion and a second non-contoured segment positioned adjacent an opposite end of said root portion, said counter-contour being positioned between said first and second non-contoured segments.

61. The abutment of claim 60, wherein said first non-contoured segment has an axial length which is greater than that of said second non-contoured segment.

62. The abutment of claim 60, wherein said second non-contoured segment has an axial length which is greater than that of said first non-contoured segment.

63. The abutment of claim 60, wherein said first non-contoured segment is flush with said second non-contoured segment.

64. The abutment of claim 59, wherein at least a portion of said counter-contour is positioned adjacent said end of said root portion remote from said neck portion.

65. An abutment, comprising a root portion sized and shaped so as to be insertable into a bore of a mating implant; a neck portion extending from said root portion, said neck portion including a screw seat in an end thereof remote from said root portion, a widened screw head section in an opposite end of said neck portion, and an internally threaded section between said screw seat and said screw head section; an inlet extending longitudinally into an end of said root portion remote from said neck portion, said inlet being sized and shaped such that a clamping screw can be inserted headfirst into said inlet through said end of said root portion remote from said neck portion; and a radially extending groove encircling said inlet and communicating therewith, said groove being sized and shaped so as to receive an expanding ring.

66. The abutment of claim 65, wherein said neck portion includes a beveled surface between said internally threaded section and said screw head section.

67. The abutment of claim 65, wherein said screw head section is in communication with said inlet.

* * * * *

UNITED STATES PATENT AND TRADEMARK OFFICE
CERTIFICATE OF CORRECTION

PATENT NO : 5,947,733
DATED : September 7, 1999
INVENTOR(S): Franz Sutter, Vincenzo Grande and Roger Tschirky It is certified that error appears in the above-identified patent and that said Letters Patent is hereby corrected as shown below:

Column 5, line 53, delete "2B" and insert -- 3B --.

Column 10, line 16, delete "1200" and insert -- 120° --.

Signed and Sealed this

Sixteenth Day of January, 2001

Attest:

Q. TODD DICKINSON

*Attesting Officer*     *Commissioner of Patents and Trademarks*

UNITED STATES PATENT AND TRADEMARK OFFICE
CERTIFICATE OF CORRECTION

PATENT NO. : 5,947,733
APPLICATION NO. : 08/836589
DATED : September 7, 1999
INVENTOR(S) : Franz Sutter, Vincenzo Grande and Roger Tschirky Page 1 of 1

It is certified that error appears in the above-identified patent and that said Letters Patent is hereby corrected as shown below:

In the Specification:

Column 5, line 53, delete "2B" and insert --3B--.

Column 10, line 16, delete "1200" and insert --120--.

Signed and Sealed this

Fifteenth Day of January, 2008

JON W. DUDAS
*Director of the United States Patent and Trademark Office*